United States Patent
Ko et al.

(10) Patent No.: US 9,510,977 B2
(45) Date of Patent: Dec. 6, 2016

(54) WOUND DRESSING

(71) Applicant: BIO-MEDICAL CARBON TECHNOLOGY CO., LTD., Taichung (TW)

(72) Inventors: Tse-Hao Ko, Taichung (TW);
Jui-Hsiang Lin, Taichung (TW);
Pei-Hsun Chou, Taichung (TW);
Yen-Ju Su, Taichung (TW)

(73) Assignee: BIO-MEDICAL CARBON TECHNOLOGY CO., LTD., Taichung (TW)

( * ) Notice: Subject to any disclaimer, the term of this patent is extended or adjusted under 35 U.S.C. 154(b) by 457 days.

(21) Appl. No.: 14/018,084

(22) Filed: Sep. 4, 2013

(65) Prior Publication Data

US 2015/0065936 A1     Mar. 5, 2015

(51) Int. Cl.
*A61F 13/00*     (2006.01)

(52) U.S. Cl.
CPC ... *A61F 13/00042* (2013.01); *A61F 13/00017* (2013.01); *A61F 13/00991* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,356,574 A | * | 10/1994 | Tamaki | D01F 9/145 264/29.2 |
| 6,673,982 B1 | * | 1/2004 | Chen | A61F 13/4751 604/378 |
| 2001/0008672 A1 | * | 7/2001 | Norvell | A41B 11/005 428/90 |
| 2010/0286584 A1 | * | 11/2010 | Areskoug | A61F 13/0213 602/46 |
| 2014/0044756 A1 | * | 2/2014 | Leung | B01D 39/1623 424/400 |
| 2015/0094672 A1 | * | 4/2015 | Blucher | A61L 15/325 604/304 |

* cited by examiner

*Primary Examiner* — Ophelia A Hawthorne
(74) *Attorney, Agent, or Firm* — Muncy, Geissler, Olds & Lowe PC

(57) ABSTRACT

A wound dressing for covering a wound is formed of at least one absorbing member and a plurality of elongated activated carbon fibers. The at least one absorbing member is made of a foamed polymeric material and includes a plurality of pores. The activated carbon fibers are distributed in the at least one absorbing member and partially protrude into the pores. Each of the activated carbon fibers has a diameter of 2-15 μm and a length of 40-1500 μm. In light of the above, the tissue fluid leaking from the wound can be absorbed by the absorbing member to prevent the wound from soakage and the activated carbon fibers inside the absorbing member can emit far-infrared rays to promote the blood circulation around the wound for quickening healing of the wound.

5 Claims, 6 Drawing Sheets

WOUND DRESSING

BACKGROUND OF THE INVENTION

1. Field of the Invention

The present invention relates generally to a wound dressing and more particularly, to a wound dressing internally containing activated carbon fibers and capable of emitting far-infrared radiation and a method of manufacturing the wound dressing.

2. Description of the Related Art

Skin is the biggest organism covering the human surface and is the first line defense for protecting the human body against infection of external pathogens and external hurt. When the skin has a wound, to make the wound heal well, a wound dressing is usually used for covering the wound empirically to provide a preferable healing environment and prevent the wound from infection.

The empirically common wound dressing, such as gauze or cotton pad, usually has the function of covering the wound and decreasing the external infection only and does not function as promoting tissue regeneration of the wound and effectively improving leakage of tissue fluid. When such conventional wound dressing is covered on a wound having more tissue fluid, it is necessary to replace the wound dressing frequently, so it is a very big burden and trouble for the patient and the healthcare personnel.

SUMMARY OF THE INVENTION

The primary objective of the present invention is to provide a wound dressing, which can absorb the liquid leaking from the wound.

Another objective of the present invention is to provide a wound dressing, which can emit far-infrared rays for helping the wound heal.

The foregoing and other objectives of the present invention are attained by the wound dressing for covering a wound. The wound dressing is formed of at least one absorbing member and a plurality of elongated activated carbon fibers. The at least one absorbing member is made of a foamed polymeric material and includes a plurality of pores. The activated carbon fibers are distributed in the at least one absorbing member and partially protrude into the pores. Each of the activated carbon fibers has a diameter of 2-15 µm and a length of 40-1500 µm.

In light of the above, the tissue fluid leaking from the wound can be absorbed by the absorbing member to prevent the wound from soakage and the activated carbon fibers in the absorbing member can emit far-infrared rays to promote blood circulation around the wound to further speed up the healing of the wound.

DETAILED DESCRIPTION OF PREFERRED EMBODIMENTS

Structural features and desired effects of the present invention will become more fully understood by reference to four preferred embodiments given hereunder. However, it is to be understood that these embodiments are given by way of illustration only, thus are not limitative of the claim scope of the present invention.

Figure 1:
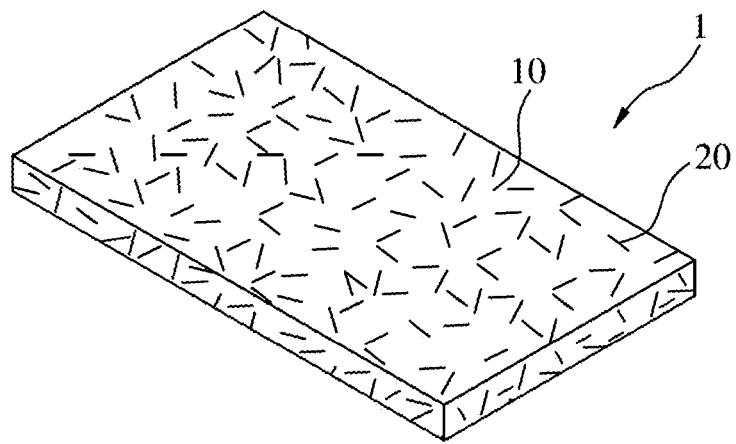
FIG. 1 is a perspective view of the first preferred embodiment of the present invention.

Referring to FIG. 1, a wound dressing 1 for covering a wound in accordance with the first preferred embodiment of the present invention is formed of an absorbing member 10 and a plurality of elongated activated carbon fibers. The detailed descriptions and operations of these elements as well as their interrelations are recited in the respective paragraphs as follows.

Figure 6:
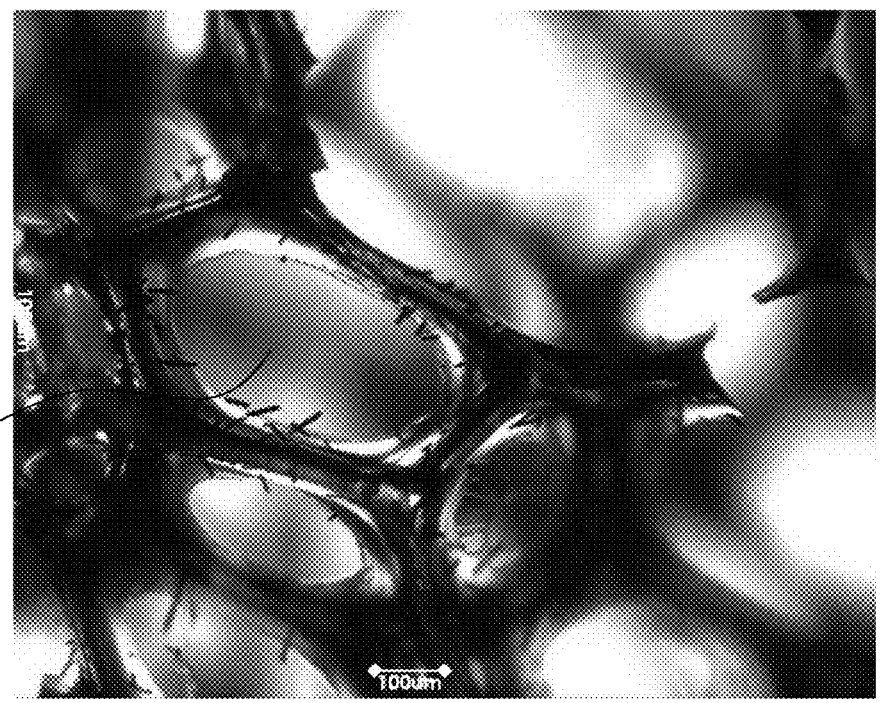
FIG. 6 is a photo showing the wound dressing of the present invention under an electromicroscope.
Figure 7:
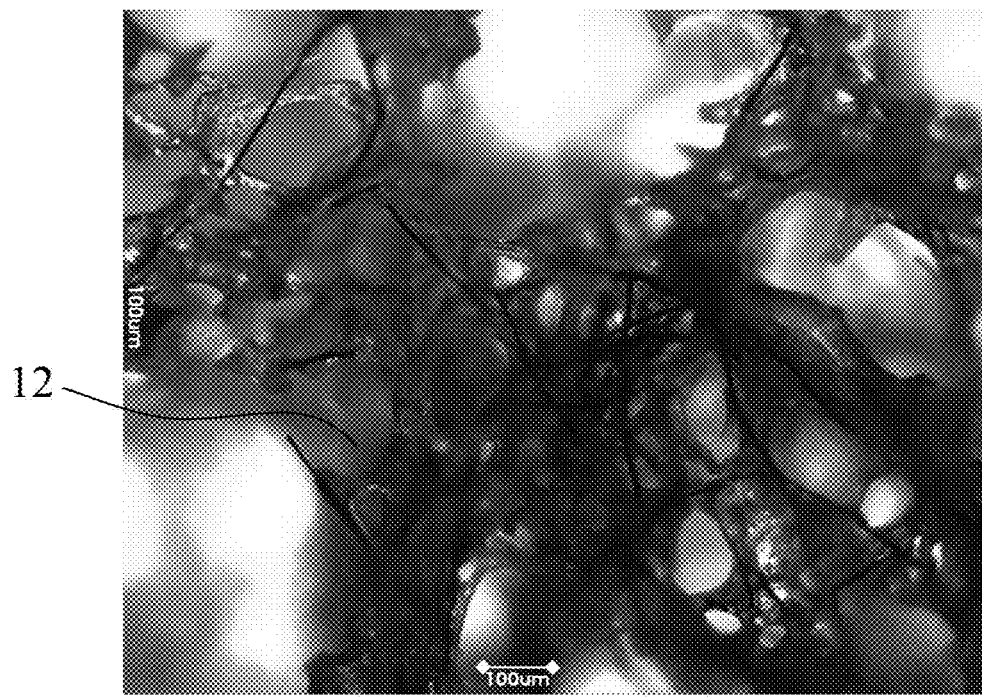
FIG. 7 is another photo showing the wound dressing of the present invention under an electromicroscope.

The absorbing member 10 is made of a foamed polymeric material and includes a plurality of pores 12, as shown in FIGS. 6 and 7. The polymeric material can be, but not limited to, polyurethane (PU) resin, polyvinyl ester resin, ethylene vinyl acetate (EVA) resin, or a mixture thereof.

The activated carbon fibers 20 are distributed in the absorbing member 10 and partially protrude into the pores 12, as shown in FIGS. 6 and 7. Each of the activated carbon fibers 20 has a diameter of 2-15 µm, preferably 4-10 µm, and a length of 40-1500 µm, preferably 40-1000 µm. If the diameter and length of the activated carbon fiber 20 are smaller than the aforesaid ranges, the activated carbon fiber 20 will be easily fully covered by the absorbing member 10 to fail to protrude into the pore 12. If the diameter and length of the activated carbon fiber 20 are larger than the aforesaid ranges, respectively, the foaming of the absorbing member 10 will be adversely affected to reduce the structural strength of the absorbing member 10 or even disable foaming of the absorbing member 10. The activated carbon fibers 20 can be, but not limited to, polyacrylonitrile-based activated carbon fibers, which can be formed by introducing polyacrylonitrile oxidized fibers into humid carbon dioxide gas under the temperature of 700-1200° C. for 1-60 minutes. Besides, the surface of the activated carbon fiber can be loaded with grains of precious metal, such as silver, gold, palladium, platinum, copper, zinc, or a mixture thereof, for antibacterial effect. Among the grains of the precious metals, the grains of silver have the best antibacterial effect.

The wound dressing 1 can be covered on the wound located on the surface of the human skin, and the absorbing member 10 having the pores 12 can absorb the tissue fluid leaking from the wound to relieve the soakage of the wound and to decrease the frequency of replacement of the wound dressing 1. After absorbing external energy, such as thermal energy or optical energy, the activated carbon fibers 20 can release the energy in the format of far-infrared rays to promote blood circulation around the wound to further help the wound heal more quickly.

Figure 2:
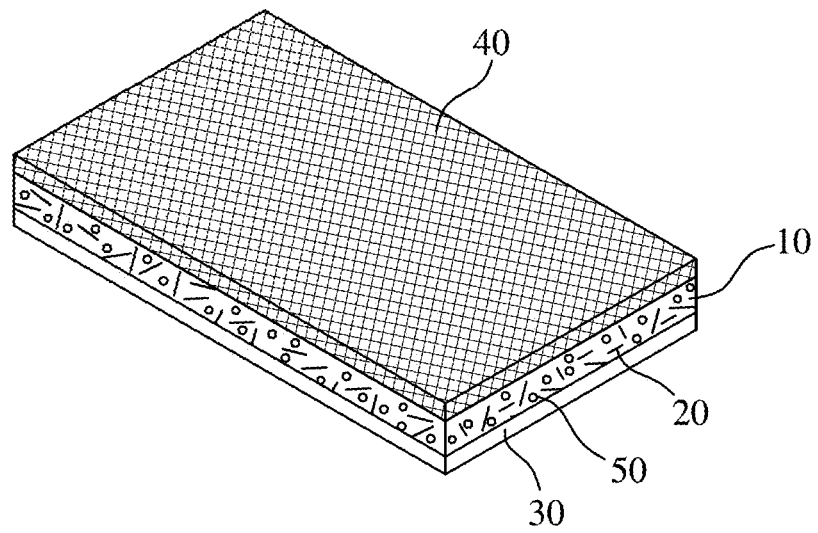
FIG. 2 is a perspective view of the second preferred embodiment of the present invention.

Referring to FIG. 2, to prevent the wound dressing 1 from sticking to the wound, the wound dressing 1 of the second preferred embodiment of the present invention further includes a contact layer 30 mounted to one side of the absorbing layer 10, which is adjacent to the wound, for contact with the wound. In addition, to prevent external source of infection from entering the wound, the wound dressing 1 can further include a breathable layer 40 mounted to one side of the absorbing layer 10, which is distant from the wound. The breathable layer 40 is made of a material, which is resistant against hydrolysis and wear and tear, easily processed, and highly flexible, and which allows mist other than any liquidized water molecule to pass through to make the surface of the wound adequately moist and make extra mist exhaust to prevent the wound from soakage.

In addition, the absorbing member 10 can further contain a therapeutic ingredient 50, which can be, but not limited to, erythromycin, tetracycline, clindamycin hydrochloride, indochlorhydroxyquin, chlorination quinoline, tolnaftate, centella asiatica, glycerol triacetane, mupirocin, povidone iodine, catechin, chitosan, polyglutamic acid, or a mixture thereof for healing trauma, burn, or scald.

Figure 3:
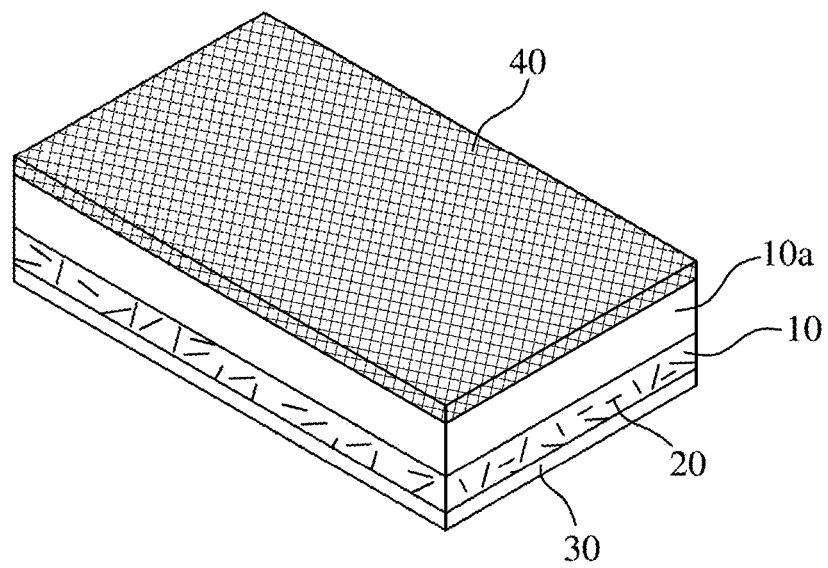
FIG. 3 is a perspective view of the third preferred embodiment of the present invention.

Referring to FIG. 3, the wound dressing 1 of the third preferred embodiment of the present invention further includes a plurality of absorbing members 10 and 10a, one of which contains the activated carbon fibers 20. In other embodiments of the present invention, the absorbing members 10 and 10a may both have the activated carbon fibers 20.

Figure 4:
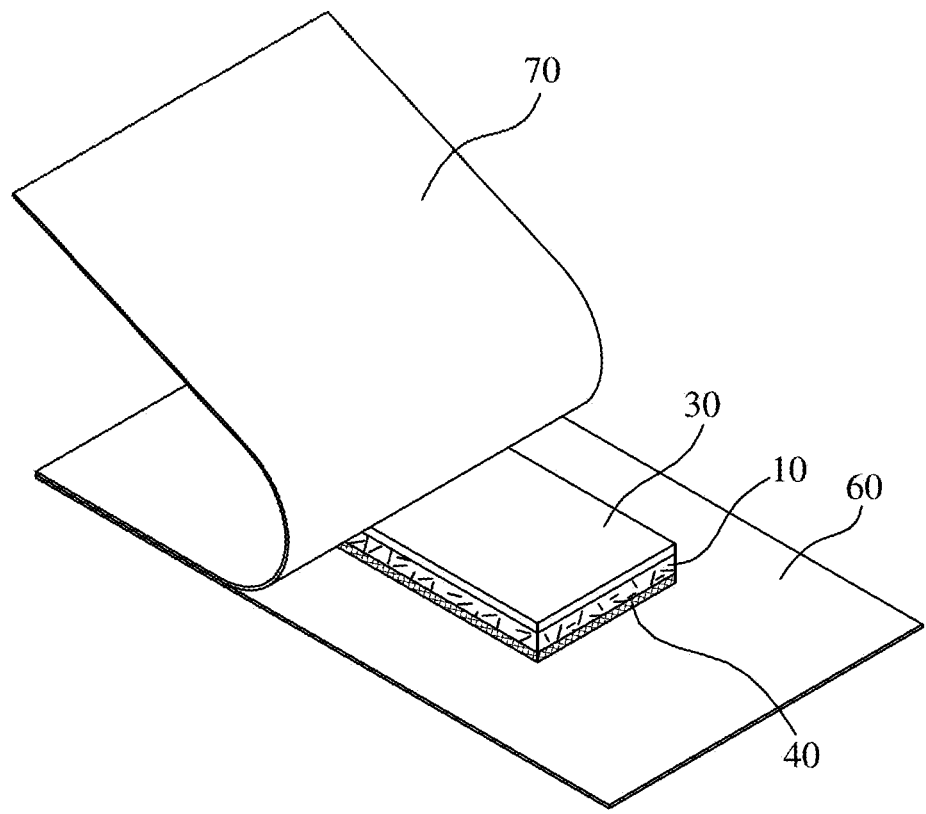
FIG. 4 is a perspective view of the fourth preferred embodiment of the present invention.

Referring to FIG. 4, the wound dressing 1 of the fourth preferred embodiment of the present invention further includes a back lining 60 mounted to one side of the breathable layer 40, which is distant from the wound. The area of the back lining 60 is larger than that of either of the contact layer 30, the absorbing member 10, and the breathable layer 40. The back lining 60 may have an area, which is not covered by the breathable layer 40 and is coated with pressure-sensitive adhesive for adhering the wound dressing 1 to the human skin. To keep the activity of the back lining 60, a release paper 70 can be covered on the pressure-sensitive adhesive on the back lining 60. The release paper 70 can be removed before the wound dressing 1 is adhered to the skin.

Figure 5:
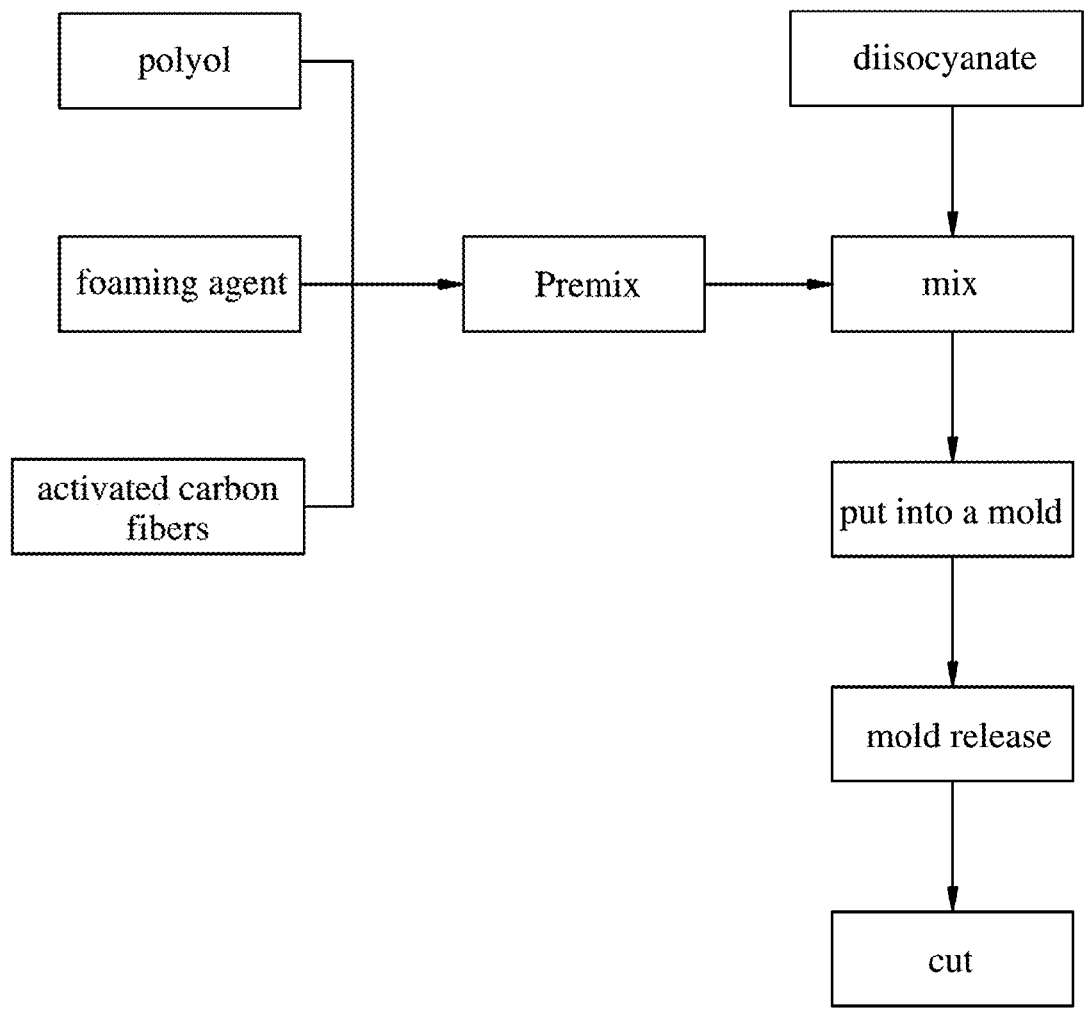
FIG. 5 is a flow chart of the method of the present invention.

Referring to FIG. 5, a method of manufacturing the primary part of the wound dressing 1 is to add the activated carbon fibers into a foam precursor of the absorbing member where the additive amount of the activated carbon fibers is 0.1-5 wt %, preferably 1-3 wt %, of the total amount of the activated carbon fibers and the foam precursor. If the additive amount of the activated carbon fibers is less than the aforesaid range, the expected effect of promoting healing of the wound will not be reached. If the additive amount of the activated carbon fibers is greater than the aforesaid range, the structural strength of the absorbing member will be easily weakened, and the absorbing member may not be successfully foam-molded. Likewise, the activated carbon fibers can be polyacrylonitrile-based activated carbon fiber formed by introducing polyacrylonitrile oxidized fiber into humid carbon dioxide gas under the temperature of 700-1200° C. for 1-60 minutes.

Under the circumstances that the absorbing member is two-component polyurethane ester, the foam precursor includes polyols (e.g. polypropylene glycol) and diisocyanates [e.g. toluene diisocyanate (TDI) or 4,4'-methylenediphenyl diisocyanate (MDI)], and foaming agent. To produce the wound dressing of the present invention, the polyols, the foaming agent, and the activated carbon fibers can be premixed. Secondly, mix the diisocyanate and the aforesaid mixture. Thirdly, put the mixture into a mold for foaming. After the foaming is completed, it can be followed by steps of mold release and cutting to produce the wound dressing of the present invention. It is worth mentioning that the foam precursor can be, but not limited to, PU resin, polyvinyl ester resin, or EVA resin.

A wound dressing of the present invention is shown in the electromicroscopic photo of FIG. 6, in which the wound dressing is made by the aforementioned method with 2 wt % of the activated carbon fibers having the diameter of 6 μm and the length of 40 μm in average.

Another wound dressing of the present invention is shown in the electromicroscopic photo of FIG. 7, in which the wound dressing is made by the afore mentioned method with 2 wt % of the activated carbon fibers having the diameter of 6 μm and the length of 1000 μm in average.

Figure 8:
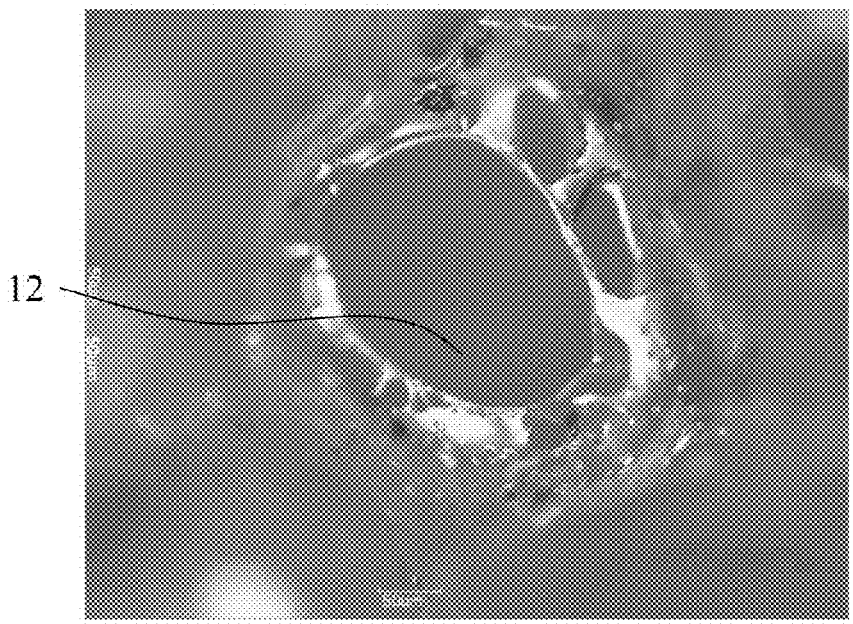
FIG. 8 is a photo showing the wound dressing of a control group under an electromicroscope.

A wound dressing of the control group is shown in the electromicroscopic photo of FIG. 8, in which the wound dressing is made by foaming the precursor with 2 wt % of the granulized activated carbon fibers having the diameter of 20 μm and the length of 35 μm in average.

Figure 9:
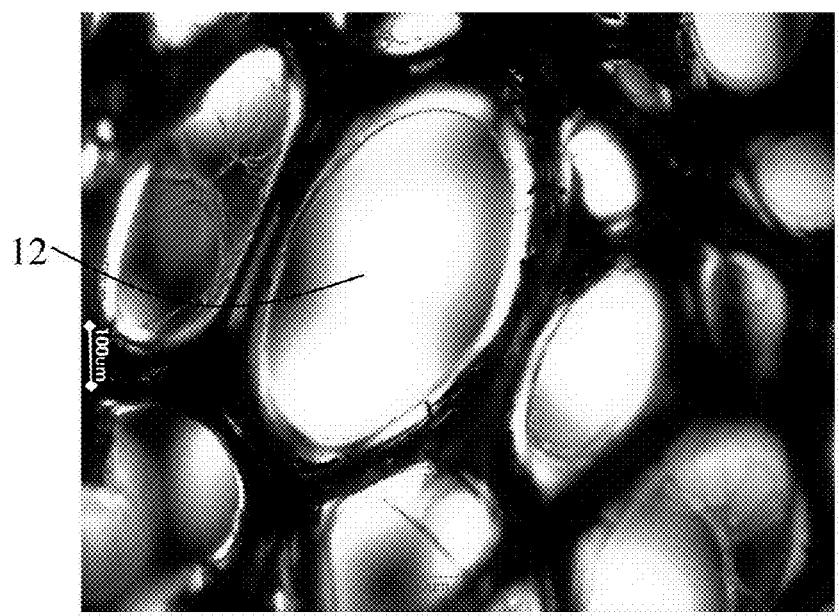
FIG. 9 is another photo showing the wound dressing of a control group under an electromicroscope.

Another wound dressing of the control group is shown in the electromicroscopic photo of FIG. 9, in which the wound dressing is made by foaming the precursor with 2 wt % of the activated carbon fibers having the diameter of 4 μm and the length of 9 μm in average.

Figure 10:
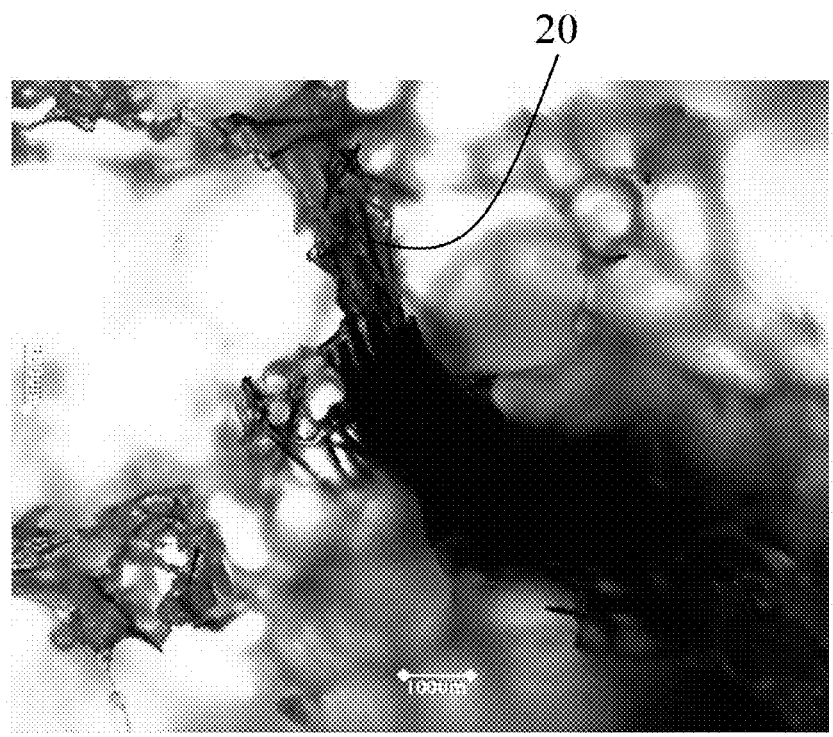
FIG. 10 is another photo showing the wound dressing of a control group under an electromicroscope.

Another wound dressing of the control group as shown in the electromicroscopic photo of FIG. 10, in which the wound dressing is made by foaming the precursor with 2 wt % of the activated carbon fibers having the diameter of 6 μm and the length of 5000 μm in average.

As known from the aforesaid electromicroscopic photos, in the wound dressing made by the method of the present invention, the absorbing member has better formability and the activated carbon fibers partially protrude into the pores of the absorbing member, as shown in FIGS. 6 and 7. Referring to FIGS. 8 and 9 again, in each of the wound dressings in the control groups, the absorbing member is though well foamed but the shorter activated carbon fibers are fully covered by the absorbing member and fail to protrude into the pores 12. Besides, in the wound dressing in the control group shown in FIG. 10, the activated carbon fibers 20 are excessively long so that they flocculate in the process of foaming and interfere with the molding of the absorbing member. Thus, the activated carbon fibers have less uniformity in the absorbing member.

In light of the above, the wound dressing of the present invention has preferable formability and high absorbability for absorbing leakage of excessive tissue fluid and can emit far-infrared rays for promoting blood circulation and quickening the healing of the wound heal. In this way, the wound dressing of the present invention can effectively shorten the time that the wound needs for healing and relieve the healthcare personnel's burden.

What is claimed is:

1. A wound dressing for covering a wound, comprising:
   at least one absorbing member made of a polymeric material and having a plurality of pores; and
   a plurality of elongated activated carbon fibers distributed in at least one of the at least one absorbing member and partially protruding into the pores, each of the activated carbon fibers having a diameter of 2-15 μm and a length of 40-1500 μm.

2. The wound dressing as defined in claim 1, wherein the activated carbon fibers are polyacrylonitrile-based activated carbon fibers.

3. The wound dressing as defined in claim 2, wherein the polyacrylonitrile-based activated carbon fibers are formed by introducing polyacrylonitrile oxidized fiber into humid carbon dioxide gas under the temperature of 700-1200° C. for 1-60 minutes.

4. The wound dressing as defined in claim 1, wherein the polymeric material is selected from a group consisting of polyurethane resin, polyvinyl ester resin, ethylene vinyl acetate resin, and a mixture thereof.

5. The wound dressing as defined in claim 1, wherein each of the activated carbon fibers has a diameter of 4-10 μm and a length of 40-1000 μm.

* * * * *